United States Patent
Herndon

(10) Patent No.: US 8,357,212 B2
(45) Date of Patent: Jan. 22, 2013

(54) BOTANICAL FUEL OXYGENATE COMPOSITIONS

(76) Inventor: Carla G Herndon, Anniston, AL (US)

( * ) Notice: Subject to any disclaimer, the term of this patent is extended or adjusted under 35 U.S.C. 154(b) by 529 days.

(21) Appl. No.: 12/542,218

(22) Filed: Aug. 17, 2009

(65) Prior Publication Data

US 2011/0035996 A1 Feb. 17, 2011

(51) Int. Cl.
*C10L 1/185* (2006.01)
*C10L 1/182* (2006.01)

(52) U.S. Cl. ............................ 44/449; 44/448; 44/451

(58) Field of Classification Search ............ 44/307, 44/449, 448, 451; 252/188.25
See application file for complete search history.

(56) References Cited

U.S. PATENT DOCUMENTS 7,029,506 B2 * 4/2006 Jordan ..................... 44/307
2006/0076535 A1 * 4/2006 Oroskar et al. ........ 252/188.25

OTHER PUBLICATIONS

Crisp, Adam: "kudzo for cars?: Researchers explore options for turning plants into ethanol" timesfreepress.com web page. Available at http://www.timesfreepress.com/news/2008/jul/06/vine-your-gas-tank/?print (first visited Oct. 11, 2008).
Nin-Hai Tseng: "Kudzu could be the next biofuel" ajc.com web page. Available at http://www.ajc.com/news/content/news/stories/2008/06/19/KUDZU_biofuel_ethanol.html (first visited Mar. 29, 2009).
Author unknown. "BP Biofuels developing advanced sustainable biofuels for transportation" BP Projects and Operations web page. Available at http://www.bp.com/sectiongeneriacarticle.do?categoryID=9025050&contentID=7046 (first visited Mar. 29, 2009).
Petiot, Emmanuel "The Important Role of Enzymes in Cellulosic Ethanol" Ethanol Producer Magazine web page. Available at http://www.ethanolproducer.com/article-print.jsp?article_id=4877; Nov. 2008 issue (first visited Nov. 1, 2008).

* cited by examiner

*Primary Examiner* — Ellen McAvoy
*Assistant Examiner* — Chantel Graham
(74) *Attorney, Agent, or Firm* — Thomas G. Peterson; Nicholas J. Landau; Bradley Arant Boult Cummings LLP

(57) ABSTRACT

Botanically derived compositions of fuel oxygenates are provided, as well as methods of making the same. The compositions are produced from extracts of plant tissues, and unexpectedly contain aliphatic ethers and alcohols in useful concentrations. These compositions represent sources of oxygenates such as MTBE, ETBE, DIPE, TAME, ETBE and TBA from non-mineral sources, allowing them to be produced domestically in countries without mineral hydrocarbon resources and allowing them to be combusted without any net addition of carbon dioxide to the atmosphere.

19 Claims, No Drawings

BOTANICAL FUEL OXYGENATE COMPOSITIONS

BACKGROUND

A. Field of the Disclosure

The present disclosure relates generally to compositions of oxygenated hydrocarbon compounds. Such compositions as well as methods for making the same are disclosed.

B. Background

Fuel oxygenates (also known simply as "oxygenates") are oxygen compounds that are added to fuels, especially gasoline, to make them burn more efficiently. Adding oxygenates to gasoline boosts the gasoline's octane level and reduces atmospheric pollution associated with fuel combustion. Commonly used fuel oxygenates are organic compounds with oxygen-containing groups, specifically hydroxyl groups and ether groups. Examples of commonly used fuel oxygenates are methyl tert-butyl ether (MTBE), tert-amyl methyl ether (TAME), diisopropyl ether (DIPE), ethyl tert-butyl ether (ETBE), tert-amyl alcohol (TAA), tert-butyl alcohol (TBA), and ethanol.

By increasing the oxygen content of the fuel, the oxygenate causes the fuel to burn more completely, creating a higher yield of carbon dioxide and lower amounts of noxious pollutants such as carbon monoxide and hydrocarbons. This is environmentally beneficial, as carbon monoxide and volatile hydrocarbons are toxic to humans, animals, and plants. Both types of compounds are directly toxic to organisms upon direct expose and are indirectly toxic due to their ability to generate tropospheric ozone. However, except for ethanol, all commonly used oxygenates are manufactured from fossil hydrocarbons such as petroleum products and natural gas products. Burning oxygenates from fossil hydrocarbons poses the same environmental threat that is posed by the burning of all fossil hydrocarbons: it causes a net increase in atmospheric carbon dioxide, which in turn increases anthropogenic global warming. There is currently a strongly felt but unmet need for fuel components such as oxygenates from sources other than fossil hydrocarbons that will not contribute to a net increase in atmospheric carbon dioxide.

There is also a long-felt but unmet need for oxygenates that can be produced in countries without large fossil fuel reserves. The commonly used oxygenates are produced at least partially from reagents that are in turn obtained from petroleum and natural gas. For example, MTBE is produced by reacting methanol (obtained from natural gas) and isobutylene (obtained from petroleum or natural gas). ETBE is produced from isobutylene and ethanol; ethanol is generally produced from biological sources, so that the burning of ETBE produces less net-carbon emissions. Countries without access to large fossil fuel reserves are forced to import fossil fuels or fossil fuel derivatives as a raw material for the production of oxygenates. This has negative economic effects on the importer, and in some cases dependence on foreign fossil fuels can undermine the importer's national security.

SUMMARY

As outlined above, there is a long-felt but unmet need in the art for fuels and fuel components that generate no net carbon dioxide upon combustion. There is also a long-felt but unmet need in the art for botanical sources of fuel oxygenate compounds that can be grown domestically in countries without large fossil fuel reserves.

The disclosure provides botanical, non-petroleum based compositions of fuel oxygenate compounds and processes of their manufacture. Because the raw material for the production of the fuel oxygenate compounds is plant material, combustion of the fuel oxygenates will introduce no net carbon dioxide into the atmosphere; as a result, these fuel oxygenates can be burned without contributing to anthropogenic global warming. Furthermore, because the source of the compounds can be grown in many environments, the disclosure eliminates the need to import petroleum or petroleum distillates as a raw material.

The present disclosure provides botanical extracts comprising hydrocarbon ethers. It has been unexpectedly discovered that extracts of plant materials contain high concentrations of hydrocarbon ether compounds that are useful as fuel oxygenates. It has also been unexpectedly discovered that such extracts contain significant amounts of aliphatic alcohols that are useful as fuel oxygenates. Such ethers and alcohols include MTBE, DIPE, TAME, ETBE, TBA, and ethanol. In some embodiments, the extracts are distilled, fermented, or both. The disclosure provides fuel oxygenates and fuel additives comprising the extract.

Some versions of these compositions will provide the advantage of allowing a country with limited oil or natural gas production to manufacture a steady supply of fuel oxygenates regardless of conditions on the global markets, such as oil embargos or increases in the prices of commodities such as crude oil and natural gas. Some versions of these compositions will provide the advantage of avoiding regulatory restrictions on fuel additives that could contribute to global warming. Another related advantage is that oxygenated fuel will be more consistently available to the consumer at less volatile prices.

DETAILED DESCRIPTION

A. Definitions

The term "MTBE" as used herein refers to methyl tert-butyl ether.

The term "DIPE" as used herein refers to diisopropyl ether.

The term "TAME" as used herein refers to tert-amyl methyl ether.

The term "ETBE" as used herein refers to ethyl tert-butyl ether.

The term "TBA" as used herein refers to tert-butyl alcohol.

The term "including" as used herein is non-limiting, and can be read to mean "including but not limited to" unless explicitly stated otherwise.

All pronouns are intended to be non-limiting. Unless otherwise stated, male pronouns encompass the female, female pronouns encompass the male, and singular pronouns encompass the plural.

B. Process of Manufacturing Botanical Fuel Oxygenates

A process for manufacturing a fuel oxygenate composition from botanical matter is provided. The composition comprises a fuel oxygenate, for example an aliphatic ether or an aliphatic alcohol. The aliphatic ether may be one or more of MTBE, TAME, and DIPE. In addition, the composition may comprise an additional aliphatic ether or an aliphatic alcohol, which may be one or more of ETBE, TBA, and ethanol. Some embodiments of the composition lack significant quantities of ethanol.

Some embodiments of the process comprise contacting a plant part with a liquid extractant to produce an extract, and incubating the extract at room temperature for an incubation period to produce an incubated product. The liquid extractant may be an aqueous extractant, for example water.

The plant material is immersed in the extractant. The plant material comprises plant parts. In an embodiment of the process, the plant is the fabaceous vine *Pueraria* sp. One common example of *Pueraria* that may be used in the process is *P. montana* var *lobata* (commonly known as "kudzu" in the United States). Examples of plant parts that may be extracted in the process are leaves, stems, and roots. These parts need not be processed prior to extraction. For ease of extraction the parts may be peeled, broken, or chopped.

After immersion, the extractant may be heated or boiled. Heating the extractant has the advantage of speeding the dissolution of extracted substances; cold extraction has the advantage of preserving extracted substances without exposing them to denaturation, vaporization, or heat-catalyzed chemical reactions. Heating may be performed at ambient or elevated pressure. If elevated pressure is desired, a sealed pressure vessel may be used. Use of elevated pressure has the advantage of allowing the extractant to be heated above its boiling point at ambient pressure; it also has the advantage of retaining volatile compounds that might otherwise escape in an open vessel. Use of ambient pressure requires less equipment, requires less energy, and provides more safety to the operator.

In some embodiments, the extract is fermented. Fermentation is mediated by a fermentative organism. The fermentative organism may be a "wild" microorganism, such as a wild yeast or wild bacterium. In this context "wild" refers to any organism that is not intentionally added to the extract in a substantially purified form. Unless the extract is sterilized (for example by boiling), those skilled in the art would expect wild fermentative organisms to be present on the botanical material and to be active during incubation given the proper conditions. Such conditions include temperature, pH, and nutrient concentrations. Conditions for fermentation can be optimized without undue experimentation by those of ordinary skill in the art. Fermentation may occur before or after heating. Fermentation after heating has the advantages of increasing the viability of the fermentative organism, which may be completely or partially killed off by the heating process. Fermentation before heating can facilitate reactions involving fermentation products that might not otherwise occur at moderate temperatures, and can also be used to halt fermentation if necessary.

In some embodiments of the process the fermentative organism is the bread and beer yeast *Saccharomnyces cerivisiae*. This yeast can be obtained from many commercial sources. For example, active dry bread yeast can be used. It will typically be activated by adding the dried yeast to a volume room-temperature water that was previously boiled, often with a small amount of dissolved sugar (such as sucrose or maltose). In such embodiments of the process the yeast in the sugar solution will be allowed to activate for a period of time before being pitched into the extract.

Once the fermentative organism has been added to the extract, fermentation will be allowed to proceed for an incubation period. The incubation period may be of a set predetermined duration, or the incubation period may depend on the occurrence of one or more events during fermentation. For example, fermentation may be allowed to continue until the density of the extract reaches a certain minimum level (or maximum level), or until the rate of production of a given fermentation product drops to a certain minimum level. In some embodiments the general appearance of the extract is used to gauge when fermentation is complete or can be stopped.

In some embodiments of the process additional sugars are added, in addition to whatever sugars are present in the plant parts. The sugar may be for example sucrose or maltose, both of which have the advantage of being available for fermentation by *S. cerivisiae*. The sugar need not be a pure or refined carbohydrate per se, but may also be a less refined cane product that is not pure sucrose, such as brown sugar or molasses. Sugar serves as a carbon source and an energy source for many fermentative organisms, under both oxic and anoxic conditions. The amount of sugar added will depend on fermentation conditions; typical sugar concentrations range from about 0.2 pounds per gallon (24 g/L) to 0.8 pounds per gallon (96 g/L). A wider range of sugar concentrations may used as well, for example from about 0 to about 0.8 pounds per gallon (about 0 to about 96 g/L).

In some embodiments of the process a supplemental additive is added to the extractant. Addition of the supplemental additive may occur prior to fermentation, as some supplemental additives affect the metabolism of the fermentative organism. Addition of the supplemental additive may also occur during fermentation. Some supplemental additives, such as enzymes, catalyze reactions that occur during heating, which may occur before or after fermentation; in such cases it is advantageous to add the supplemental additive such that it will be present during the heating of the extract (before or after fermentation).

The supplemental additive may be an enzyme. The enzyme may function to aid fermentation by producing nutrients in the extract, for example by hydrolyzing long-chain chain polymers into more readily available short polymers or monomers. Examples of enzymes that can be added as supplemental additives include amylase (which produces glucose from starch), proteases (which hydrolyze proteins), and lipases (which hydrolyze ester bonds in lipids). Exemplary proteases include bromelain, papain, and pepsin. The supplemental additive may also be a plant material that is the source of an enzyme; for example, pineapple may be added as a source of bromelain, or papaya may be added as a source of papain. Other supplemental additives include botanical oils, betaine salts, and cellulose.

Some embodiments of the method comprise distilling an extract of a plant part to produce a vapor comprising a fuel oxygenate, condensing at least of portion of the fuel oxygenate, and collecting the portion of the fuel oxygenate. The extract may be any of the extracts disclosed herein produced by any of the processes disclosed herein, or other extracts of plant parts comprising a fuel oxygenate.

The distillation is conducted at a distillation temperature at which some components are vaporized to a greater extent than are others. The distillation temperature must be sufficient to at least partially vaporize the fuel oxygenate. In some embodiments of the process, the distillation temperature is about 60 to about 95° C., or exactly 60-95° C. Some embodiments of the process comprise a distillation temperature of up to about 100° C.

The distillation step may comprise reflux condensation. Reflux condensation is a method comprising directing the vapor through a reflux condenser positioned above the still pot, causing less volatile components of the vapor to condense and fall back to the still pot as liquid, where they are again vaporized. The result is that a purer distillate is obtained in the still receiver.

C. Botanical Extracts

The disclosure provides botanical extracts comprising an oxygenate. The extract may be a raw extract or a processed extract. For example, the processed extract may be a fermented extract or a distilled extract.

In some embodiments of the extract the oxygenate is one of MTBE, DIPE, and TAME. Some embodiments of the extract further comprise an additional oxygenate, for example ethanol, ETBE, and TBA. Some embodiments of the extract do not comprise a significant amount of ethanol.

The extract may be produced by any of the manufacturing methods described herein and using any of the plants and plant parts described herein.

The extract may contain oxygenates in various relative concentrations. In some embodiments of the extract, the ratio of ethanol to MTBE (expressed as the v/v concentration of ethanol divided by the v/v concentration of MTBE in the product) is about 0% to about 65.4%; the ratio of ETBE to MTBE is about 0% to about 8.7%; the ratio of TAME to MTBE is about 7.8% to about 53.0%; the ratio of DIPE to MTBE is about 12.6% to about 106.0%; the ratio of TBA to MTBE is about 0% to about 117.5%. The product may contain oxygenates in various absolute concentrations. In some embodiments of the extract, the oxygenates are present in the following ranges of concentrations (expressed in terms of volume/volume concentration): ethanol, about 0% to about 20.2%; MTBE, about 26.8% to about 57.7%; ETBE, about 0% to about 2.7%; TAME, about 2.4% to about 14.2%; DIPE, about 3.9% to about 28.4%; and TBA, about 0% to about 36.3%. Some embodiments of the extract have an octane rating of about 108.

D. Fuel Oxygenate Compositions and Fuel Additives

The disclosure provides a fuel oxygenate composition comprising the product of any of the processes disclosed herein. The product of the process comprises an oxygenate. In some embodiments the oxygenate is MTBE, DIPE, or TAME. In some embodiments, the product comprises MTBE, DIPE, and TAME. In further embodiments, the product of the process comprises an additional oxygenate selected from the group consisting of ethanol, ETBE, and TBA. In some embodiments the product of the process does not comprise a significant amount of ethanol. In this context, a "significant amount" is an amount that can be practically employed as a fuel or an oxygenate.

The product of the process may contain oxygenates in various relative concentrations. In some embodiments of the product, the ratio of ethanol to MTBE (expressed as the v/v concentration of ethanol divided by the v/v concentration of MTBE in the product) is about 0% to about 65.4%; the ratio of ETBE to MTBE is about 0% to about 8.7%; the ratio of TAME to MTBE is about 7.8% to about 53.0%; the ratio of DIPE to MTBE is about 12.6% to about 106.0%; the ratio of TBA to MTBE is about 0% to about 117.5%. The product may contain oxygenates in various absolute concentrations. In some embodiments of the product, the oxygenates are present in the following ranges of concentrations (expressed in terms of volume/volume concentration): ethanol, about 0% to about 20.2%; MTBE, about 26.8% to about 57.7%; ETBE, about 0% to about 2.7%; TAME, about 2.4% to about 14.2%; DIPE, about 3.9% to about 28.4%; and TBA, about 0% to about 36.3%. Some embodiments of the product have an octane rating of above 108.

The disclosure provides a fuel oxygenate composition comprising any of the botanical extracts provided herein. The disclosure provides a fuel additive comprising any of the fuel oxygenate compositions provided.

E. Examples

1. Example 1

Fresh kudzu was cut from a living vine and washed. The kudzu was placed in a 10 gallon extraction vessel, in which it occupied about 75% of the volume. The vessel was filled with water extractant. The mixture was boiled for 20 minutes, and 8 pounds of refined table sugar (sucrose) were added to the boiled mixture. One packet of wine yeast (Red Star Champaign yeast) was added to 1 cup of previously boiled water. One teaspoon of sucrose was added to the yeast suspension and incubated for 30 minutes.

The boiled extract was allowed to cool, and the yeast were pitched. The extract was allowed to ferment in an airtight container for six days. There was no significant change in specific gravity during fermentation.

The fermentate was filtered to remove the plant material, and the filtrate was distilled. The initial distillation temperature was 60° C., and was slowly increased to 95° C. Distillation appeared to be complete after about six hours. The distillate was analyzed using a volatile organic compound (VOC) fuel analyzer. Surprisingly, no ethanol was detected. The distillate was 28.6% MTBE by volume, 14.4% TAME by volume, and 30.0% DIPE by volume.

2. Example 2

Fresh kudzu was obtained from a living vine. The leaves and stems were chopped and added to 24 ounces of water. Larger stems were cut to fit into a 10 gallon vessel, and covered with 64 ounces of water. The chopped leaves and stems were combined with the larger stems. Two pounds of refined white table sugar (sucrose) was dissolved in 12.8 ounces of boiling water and allowed to cool. The cooled sugar solution was then added to the mixture of kudzu and water in the 10 gallon vessel. Yeast were pitched and one root of the plant 18" long was coarsely cut and added to the vessel. The vessel was covered with an airtight lid and fermentation was allowed to proceed for seven days. The fermentate was distilled by reflux distillation and three gallons of distillate were collected of golden yellow color. The distillate was analyzed using a volatile organic compound (VOC) fuel analyzer. Surprisingly, no ethanol was detected. The distillate was 26.8% MTBE by volume, 14.2% TAME by volume, and 28.4% DIPE by volume.

3. Example 3

Two pounds of kudzu root were added to 2 quarts of water in a pressure cooker. Two capsules of enzyme supplement were added to the water and root mixture. Based on the labeling of the supplements, the contents were as follows: 200 mg betaine hydrochloride, 20,000 units amylase, 20,000 units protease, 3,400 units lipase, 100 mg cholic acid, 50 mg bromelain, 50 mg papain, 50 mg pepsin, 45 mg papaya, 10 mg cellulose, and 45 mg pineapple. Vegetable oil was added to the mixture and the mixture was boiled for one hour. After 24 hours an additional two capsules of supplement was added to the mixture in one quart of water and the mixture was boiled for 30 minutes. After cooling the mixture was cooled and transferred to a 10 gallon still pot. Ten ounces brown sugar and 2 pounds refined white table sugar (sucrose) were added to the mixture and allowed to ferment for 21 days. The fermentate was distilled by reflux distillation at 70-80° C. The distillate was analyzed using a volatile organic compound (VOC) fuel analyzer. The distillate was 20.2% ethanol by volume, 30.9% MTBE by volume, 2.7% ETBE by volume, 2.4% TAME by volume, 3.9% DIPE by volume, and 36.3% TBA by volume.

4. Example 4

The stems, leaves, and smaller roots of a kudzu vine were placed in a fermentation vessel with 5 gallons of water and 4 supplement capsules. Yeast were pitched after 24 hours. After 21 days of fermentation the fermentate was distilled by reflux distillation at 80-90° C. The distillate was analyzed using a volatile organic compound (VOC) fuel analyzer. The distillate was 14.5% ethanol by volume, 44.5% MTBE by volume, 0% ETBE by volume, 10.5% TAME by volume, 12.0% DIPE by volume, and 23.7% TBA by volume.

5. Example 5

The roots, stems and leaves of a kudzu vine were immersed in water. Two pounds of refined cane sugar (sucrose) was added to the mixture, followed by two packets of dried baking yeast. The vessel was sealed and fermentation was allowed to proceed for three days. The fermentate was reflux-distilled by heating the fermentate to 80-90° C. and collecting the distillate. The temperature was slowing increased to 100° C. Distillation proceeded for five hours. Two samples of distillate were analyzed using a volatile organic compound (VOC) fuel analyzer. The first sample of distillate was 3.0% ethanol by volume, 57.7% MTBE by volume, 0.6% ETBE by volume, 10.0% TAME by volume, 25.1% DIPE by volume, and 9.3% TBA by volume. The second sample of distillate was 2.7% ethanol by volume, 55.0% MTBE by volume, 1.7% ETBE by volume, 13.7% TAME by volume, 25.1% DIPE by volume, and 8.8% TBA by volume.

F. Conclusions

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein.

I claim:

1. A fuel additive composition comprising an aqueous extract of kudzu, said extract comprising at least one oxygenate selected from the group consisting of: MTBE, DIPE, and TAME.

2. The fuel additive composition of claim 1 wherein MTBE, DIPE, and TAME are present in the extract.

3. The fuel additive composition of claim 1, wherein the extract further comprises an oxygenate selected from the group consisting of: ethanol, ETBE, and TBA.

4. The fuel additive composition of claim 1, wherein the extract is a distilled extract, a fermented extract, or a combination thereof.

5. The fuel additive composition of claim 1, wherein MTBE and DIPE are present in the extract, and wherein the volume-to-volume ratio of DIPE to MTBE in the extract is from about 13% to about 106%.

6. The fuel additive composition of claim 1, wherein MTBE and TAME are present in the extract, and wherein the volume-to-volume ratio of TAME to MTBE in the extract is from about 8% to about 53%.

7. The fuel additive composition of claim 3, wherein MTBE and ethanol are present in the extract, and wherein the volume-to-volume ratio of ethanol to MTBE in the extract is from above about 0% to about 65%.

8. The fuel additive composition of claim 3, wherein MTBE and ETBE are present in the extract, and wherein the volume-to-volume ratio of ETBE to MTBE in the extract is from about 0% to about 9%.

9. The fuel additive composition of claim 3, wherein MTBE and TBA are present in the extract, and wherein the volume-to-volume ratio of TBA to MTBE in the extract is from above about 0% to about 118%.

10. A fuel additive composition, comprising a fuel oxygenate composition from kudzu, said composition comprising a fuel oxygenate other than ethanol, made by the process comprising:
   a. contacting a part of a kudzu plant with a liquid extractant to produce an extract; and
   b. incubating the extract at room temperature for an incubation period to produce an incubated product.

11. The fuel additive composition of claim 10, wherein the fuel oxygenate is an ether.

12. The fuel additive composition of claim 10 wherein the liquid extractant is an aqueous extractant.

13. The fuel additive composition of claim 10, wherein the incubating step further comprises fermenting the extract with a fermentative organism.

14. The fuel additive composition of claim 13, wherein the fermentative organism is a yeast of the species *Saccharomyces cerivisiae*.

15. The fuel additive composition of claim 10, wherein a sugar is dissolved in the liquid extractant.

16. The fuel additive composition of claim 10, wherein a supplemental additive is present in the liquid extractant, said supplemental additive being selected from the group consisting of: a botanical oil, a betaine salt, amylase, protease, lipase, cholic acid, bromelain, papain, pepsin, papaya, pineapple, and cellulose.

17. The fuel additive composition of claim 10, further comprising bringing the extract to a boil before incubating the extract at room temperature.

18. The fuel additive composition of claim 10, wherein the fuel oxygenate is selected from the group consisting of: MTBE, ETBE, TAME, DIPE and TBA.

19. The fuel additive composition of claim 18, wherein the fuel oxygenate is selected from the group consisting of: MTBE, TAME, and DIPE.

* * * * *